(12) United States Patent
Wagner

(10) Patent No.: US 10,299,745 B2
(45) Date of Patent: May 28, 2019

(54) TRACEABLE DEVICES FOR GASTROINTESTINAL USE AND METHODS OF USE AND MANUFACTURING THE SAME

(71) Applicant: Loyola University of Chicago, Maywood, IL (US)

(72) Inventor: Robert Hans Wagner, Burr Ridge, IL (US)

(73) Assignee: Loyola University of Chicago, Maywood, IL (US)

( * ) Notice: Subject to any disclaimer, the term of this patent is extended or adjusted under 35 U.S.C. 154(b) by 532 days.

(21) Appl. No.: 14/980,468

(22) Filed: Dec. 28, 2015

(65) Prior Publication Data

US 2016/0184466 A1 Jun. 30, 2016

Related U.S. Application Data

(60) Provisional application No. 62/097,193, filed on Dec. 29, 2014.

(51) Int. Cl.
| | | |
|---|---|---|
| *A61K 49/04* | (2006.01) | |
| *A61B 6/00* | (2006.01) | |
| *B29C 70/80* | (2006.01) | |
| *B29C 70/88* | (2006.01) | |
| *A61B 90/00* | (2016.01) | |
| *B29K 91/00* | (2006.01) | |
| *B29L 31/00* | (2006.01) | |

(52) U.S. Cl.
CPC .......... *A61B 6/4258* (2013.01); *A61B 6/4057* (2013.01); *A61B 6/50* (2013.01); *A61B 6/5217* (2013.01); *A61B 90/39* (2016.02); *B29C 70/80* (2013.01); *B29C 70/88* (2013.01); *A61K 49/0495* (2013.01); *B29K 2091/00* (2013.01); *B29L 2031/753* (2013.01)

(58) Field of Classification Search
None
See application file for complete search history.

(56) References Cited

U.S. PATENT DOCUMENTS

| | | | |
|---|---|---|---|
| 2,540,979 A * | 2/1951 | Clymer | A61K 9/282 |
| | | | 424/476 |
| 4,115,540 A | 9/1978 | Digenis | |
| 4,243,652 A | 1/1981 | Francis | |
| 4,349,529 A | 9/1982 | Morcos et al. | |
| 4,453,929 A | 6/1984 | Silverman et al. | |
| 4,657,755 A | 4/1987 | Christensen et al. | |
| 5,686,113 A * | 11/1997 | Speaker | A61K 9/1652 |
| | | | 424/490 |
| 5,697,384 A | 12/1997 | Yutaka et al. | |
| 6,432,382 B1 | 8/2002 | Mehta | |
| 7,787,926 B2 | 8/2010 | Kimchy | |
| 7,869,856 B2 | 1/2011 | Moshe | |
| 8,852,083 B2 | 10/2014 | Mintchev et al. | |
| 2004/0013626 A1 * | 1/2004 | Gref | A61K 9/167 |
| | | | 424/70.13 |
| 2006/0034758 A1 * | 2/2006 | Babich | A61K 51/0478 |
| | | | 424/1.11 |
| 2009/0312627 A1 | 12/2009 | Matott et al. | |
| 2013/0017262 A1 * | 1/2013 | Mullen | A61K 9/2018 |
| | | | 424/465 |

FOREIGN PATENT DOCUMENTS

WO 1983003762 10/1983

OTHER PUBLICATIONS

Alrefae et al. (J. Assoc. Arab Univ. Basic Appl. Sci. 2013, 13, 24-27).*
FoodHappy 2012, pp. 1-4.*
Yamada et al. (Soil Science & Plant Nutrition 2005, 51, 141-145).*
Bhaledar M, (Ancient science of life 2004, XXVI, 52-55).*
Camilleri et al., Toward a Relatively Inexpensive, Noninvasive, Accurate Test for Colonic Motility Disorders, In Gastroenterology 1992; 103: 36-42.
Burton et al., Colonic Transit Scintigraphy Labeled Activated Charcoal Compared withIon Exchange Pellets; Journal of Nuclear Medicine 1997; 38: 1807-1810.
Szarka et al., Methods for the Assessment of Small Bowel and Colonic Transit, Semin. Nucl. Med. Mar. 2002; 42 (2): 113-123.
Guang-Uei Hung, Chien-Chung Tsai and Wan-Yu Lin, "Development of a new method for small bowel transit study", Annals of Nuclear Medicine, vol. 20, No. 6, 387-392, 2006.
Hala M. Fadda, Emma L. McConnell, Michael D. Short, and Abdul W. Basit, "Meal-Induced Acceleration of Tablet Transit Through the Human Small Intestine", Pharmaceutical Research, vol. 26, No. 2, Feb. 2009.
A. McDowell, J.J. Nicoll, B.J. McLeod, I.G. Tucker, N.M. Davies, Gastrointetinal transit in the common brushtail possum measured by gamma scintigraphy, International Journal of Pharmaceuticals, Sep. 30, 2005; 125-132.
PCT International Search Report dated May 13, 2016.

* cited by examiner

*Primary Examiner* — Michael G. Hartley
*Assistant Examiner* — Melissa J Perreira
(74) *Attorney, Agent, or Firm* — Hartman Global IP Law; Gary M. Hartman; Domenica N. S. Hartman

(57) ABSTRACT

A traceable device and procedure suitable for investigating gastrointestinal motility disorders by measuring transit time of the device as it is passed through the gastrointestinal tract of a patient. The device includes a core material configured to be imaged with a gamma imaging process and optionally also an x-ray imaging process, and a sealing material substantially insoluble in gastrointestinal fluids and fully encapsulating the core material.

5 Claims, 3 Drawing Sheets

TRACEABLE DEVICES FOR GASTROINTESTINAL USE AND METHODS OF USE AND MANUFACTURING THE SAME

CROSS REFERENCE TO RELATED APPLICATIONS

This application claims the benefit of U.S. Provisional Application No. 62/097,193, filed Dec. 29, 2014, the contents of which are incorporated herein by reference.

BACKGROUND OF THE INVENTION

The present invention generally relates to medical imaging procedures and to devices and pharmaceuticals capable of use therewith. The invention particularly relates to medical imaging techniques that utilize devices that exhibit a sufficient level of radioactivity for use as tracers in imaging a patient's gastrointestinal tract.

A variety of gastrointestinal motility disorders are known that can affect the movement of food as it passes through the human body from stomach through excretion. Dysmotility symptoms are generally inconsistent, and may include bloating, abdominal pain, nausea and vomiting, diarrhea, and/or constipation. A commonly used procedure in nuclear medicine is a gastric emptying study which measures the rate of emptying from the stomach into the small bowel (intestine). Using a standard physiologic meal (per the Society of Nuclear Medicine and Molecular Imaging guidelines) that is tagged with a radioactive tracer, an amount of material emptied from a subject's stomach over a period of time can be accurately determined to identify the presence of dumping syndrome, gastroparesis, and potentially other gastrointestinal disorders. The amount of radiation used is relatively small and allows for imaging at various times, typically up to four hours after consuming a meal. Imaging of the small and large bowels, however, requires different techniques.

A radiographic small bowel follow-through study can determine the passage of radio-opaque material (for example, materials comprising iodine or barium) through the small bowel and into the large bowel. This procedure requires serial imaging of the abdomen. Barium in particular tends to extend along the length of the small bowel as the barium mixes with food, rather than remaining intact as a point source. While this allows for good visualization of the anatomy of the small bowel, it may not accurately reflect the transit time of a food particle.

Transit through the small and large bowels has been performed using a resin compound (*Toward a Relatively Inexpensive, Noninvasive, Accurate Test for Colonic Motility Disorders,* Camilleri et al., In Gastroenterology 1992; 103:36-42) or activated charcoal labeled with an isotope and placed into a gelatin capsule (*Colonic Transit Scintigraphy Labeled Activated Charcoal Compared with Ion Exchange Pellets,* Burton et. al., Journal of Nuclear Medicine 1997; 38:1807-1810). Notably, the use of a resin compound requires an Investigational New Drug Application (IND) from the US Food and Drug Administration (FDA). In regards to the activated charcoal, the capsule may be subsequently enteric coated and then administered to the subject. Using a standard nuclear medicine gamma camera, this radioactive capsule can be followed through the small bowel. When the capsule reaches the large bowel the enteric coating and capsule dissolves, releasing the tracer into the colon. Measurement of the large bowel transit however is complicated by mixing of the tracer with the bowel contents. A percentage of tracer activity needs to be calculated in the ascending, transverse, descending and sigmoid colon. Furthermore, activated charcoal can be difficult to work with and the process of enteric coating can be demanding and time consuming. Additional assessment methods are thoroughly described in *Methods for the Assessment of Small Bowel and Colonic Transit,* Szarka et al., Semin. Nucl. Med. 2002 March; 42(2):113-123), the contents of which are incorporated herein by reference.

Measuring transit through the small and large bowels using a resin compound or activated charcoal requires the attention of a radiopharmacist and the radioactive tracers are conventionally produced locally for their own institutions. There are no known comparable products available from a commercial radiopharmacy.

In view of the above, it can be appreciated that there are certain problems, shortcomings or disadvantages associated with the prior art, and that it would be desirable if improved methods, devices, and pharmaceuticals were available for investigating gastrointestinal motility disorders, particularly if capable of remaining as a point source through the small and large bowels of a subject.

BRIEF DESCRIPTION OF THE INVENTION

The present invention provides medical imaging procedures, traceable devices that exhibit a detectable level of radioactivity, and methods of manufacturing the devices, wherein the devices and procedures are suitable for investigating gastrointestinal motility disorders by measuring transit time from the stomach through the small and large bowels of a subject.

According to one aspect of the invention, a traceable device configured to be administered to a patient and passed through the gastrointestinal tract of the patient includes a core material configured to be imaged with a gamma imaging process and optionally also an x-ray imaging process, and a sealing material substantially insoluble in gastrointestinal fluids and fully encapsulating the core material.

According to another aspect of the invention, a traceable device includes a core material comprising a radioactive isotope visible with a gamma imaging process and a sealing material substantially insoluble in gastrointestinal fluids and fully encapsulating the core material.

Another aspect of the invention is a method of manufacturing the traceable device described above including applying the radioactive isotope to the core material, and encapsulating the core material in the sealing material.

Another aspect of the invention is a method of measuring a transit time of the traceable device of described above through at least a portion of the gastrointestinal tract of a patient including orally administering the device to the patient, obtaining at least one image of the patient to locate the device, and measuring the transit time of the device through the portion of the gastrointestinal tract with the at least one image and at least a second image of the device within patient.

A technical effect of the invention is the ability to more accurately measure transit time from the stomach and through the small and large bowels of a patient. In particular, it is believed that by encapsulating the radioactive isotope in an indigestible sealing material, the likelihood of the isotope remaining a point source rather than being dispersed through the patient's gastrointestinal tract will be increased, particularly through the small and/or large bowel, or even all the way through the body of the patient.

Other aspects and advantages of this invention will be better appreciated from the following detailed description.

DETAILED DESCRIPTION OF THE INVENTION

The present invention relates to medical imaging procedures and provides radioactive pharmaceuticals (radiopharmaceuticals) and devices for use as tracers in imaging a patient's gastrointestinal tract, as well as methods for manufacturing the devices. Preferably, the devices (at times referred to herein as traceable devices) are capable of passing through a patient's gastrointestinal tract without dispersing, that is, the devices remain intact as a point source, and therefore may be more accurately and reliably imaged relative to conventional procedures. The devices described hereinafter may be administered to and imaged in a patient according to conventional methods common in the art, and therefore administration and imaging techniques will not be discussed further herein.

Figure 1:
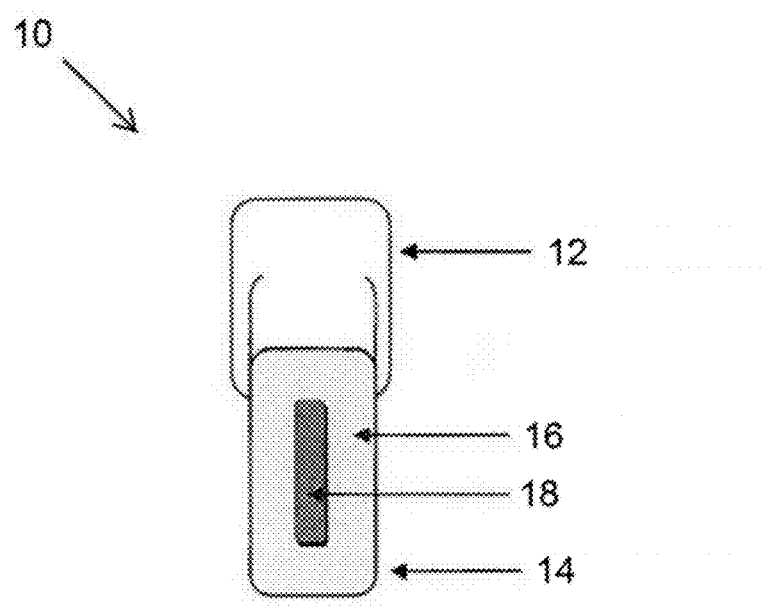
FIG. 1 represents a nonlimiting embodiment of a traceable device in accordance with certain aspects of the present invention.

FIG. 1 represents a nonlimiting embodiment of a traceable device 10 according to an aspect of the invention. The device 10 includes a core material 18 that is formed of any material or combination of materials, at least one of which is detectable by a gamma imaging procedure while located in the gastrointestinal tract. For example, the core material 18 may comprise a naturally radioactive material and/or a material processed to be radioactive (collectively referred to herein as radioactive materials) and traceable with a gamma imaging process. The radioactive material may also be traceable with another imaging process, for example, an x-ray imaging process, and/or the core material 18 may further comprise one or more additional materials that are traceable by x-ray imaging or another imaging process. The radioactive material may be any known isotope suitable for medical imaging. Nonlimiting examples include isotopes of gallium, thallium, and indium. Although depicted as comprising a single core material 18 in FIG. 1, it is foreseeable and within the scope of the invention that the device 10 may comprise one or more core materials 18. For example, the core material 18 of the device 10 could comprise a first core material comprising a radioactive isotope as well as a nonradioactive second core material comprising a metallic or high density material that is radio-opaque, that is, sufficiently dense so as to exhibit relative opacity to, or impenetrability by, x-rays such that the material is visible by x-ray imaging techniques while in the gastrointestinal tract. In such instances, the device 10 could be imaged using a combination of imaging techniques, for example, a gamma imaging technique and additionally an x-ray imaging technique. Such combination imaging procedures could similarly be achieved with a single core material 18 comprising a radioactive metallic or otherwise radio-opaque material. In either case, radio-opacity of the core material 18 (or a portion thereof) can be used to confirm that the device 10 has exited the patient, a particularly advantageous capability if the radioactive material has a relatively short half-life and the possibility exists that the device 10 might no longer be detectible by gamma imaging before it is excreted from the patient's body. Such confirmation can be further useful to ensure that the device 10 has not become lodged in a diverticula or the appendix.

The core material 18 is enclosed, fully encapsulated, and sealed in sealing material 16. The sealing material 16 ensures or increases the likelihood that the core material 18 will remain intact as a point source while passing through a patient's gastrointestinal tract, or at least a portion thereof being tested, rather than being dispersed. Therefore, the sealing material 16 may be formed of any material that is substantially indigestible, in other words, substantially insoluble and/or unaffected by stomach acid, fluids, or enzymes that are present throughout the entire gastrointestinal tract, such that the core material 18 remains intact as a point source to or through a desired area of the gastrointestinal tract being tested, such as the small and/or large bowel. Nonlimiting examples of materials suitable as the sealing material 16 may include various inert and/or non-digestible waxes and polymers.

Optionally, the sealing material 16 may be enclosed in an outer capsule (for example, the combination of a cap 12 and body 14 represented in FIG. 1) that is optionally but preferably formed of one or more gelatin materials that are readily digestible by stomach acid or enzymes present in the gastrointestinal tract. The capsule 12/14 is especially useful in forming and maintaining the shape of the device 10 if the sealing material 16 is composed of a relatively soft and malleable material such as a wax. In contrast, if the sealing material 16 comprises a relatively rigid material, the outer capsule 12/14 may be unnecessary. If used, the outer capsule 12/14 preferably defines a body of the device 10.

The traceable device 10 may be of any size or shape that can be introduced into the gastrointestinal tract of a patient. If administered orally, the device 10 is preferably sized and shaped in a manner suitable for promoting ease of swallowing by the patient. The device 10 may be administered alone or in conjunction with other materials conventionally used for gastrointestinal studies. The device 10 may be administered to the patient and subsequently imaged as it moves through a patient's gastrointestinal tract. According to preferred but nonlimiting embodiments of the invention, the device 10 has a lower specific gravity than barium and other radio-opaque metals that have been used or might otherwise be suitable for placement in the gastrointestinal tract. A relatively low specific gravity promotes the ability of the device 10 to more closely mimic or otherwise remain entrained in food concurrently present in the gastrointestinal tract. The specific gravity of the device 10 may also be standardized for a given investigation such that results are not altered by variations in specific gravity between trials of the investigation.

The core material 18 may comprise any amount of radioactive isotope that is within safety guidelines for conventional medical imaging techniques. As an example, a core material 18 providing a dosage of less than about 0.2 millicuries is believed to be acceptable. As a non limiting example, a dosage level in a range of about 0.1 to 0.2 milicurries or in a lower range of about 0.05 to 0.15 millicuries may be suitable if gallium-67 is used as the radioactive isotope. As discussed below, doses of gallium-67 in the latter range were successfully used during initial investigations leading to the present invention, and further investigations have successfully used still lower radioactivity levels. The lower limit for the radioactivity level of the isotope is generally going to be limited at least in part by the type of imaging camera used to track the device 10, with more sensitive cameras allowing for the use of lower radioactivity levels. Dosages of less than about 0.2 millicuries provide significantly less radiation exposure to patients relative to conventional imaging techniques. For example, oral administration of the device 10 comprising a dose of gallium-67 of about 0.1 to 0.2 millicuries would result in only about 25 percent to about 50 percent of the radiation exposure to the bowel that would be estimated to be caused by a standard gallium scan. For example, a standard gallium scans may entail injecting a dose of about five to seven millicuries of the gallium-67 isotope, and approximately 9 percent of the isotope is normally excreted into the bowel. A dose estimate of radiation from a five-millicurie dose of injected gallium-67 to the bowel wall is estimated to result in about 1.1 rad absorbed by the stomach, about 1.8 rad absorbed by the small bowel, about 2.8 rad absorbed by the upper large bowel, and about 4.5 rad absorbed by the lower large bowel. Consequently, if 9 percent of a five-millicurie injected gallium dose is excreted through the bowel (from package insert data), the estimated millicurie amount excreted is estimated to be about 0.45 millicuries. In contrast, if the device 10 comprises a dose of gallium-67 of about 0.1 to 0.2 millicuries, estimated dosimetry to the normal gastrointestinal tract with the device 10 is estimated to be about 0.275 to about 0.55 rad absorbed by the stomach, about 0.45 to about 0.9 rad absorbed by the small bowel, about 0.7 to about 1.4 rad absorbed by the upper large bowel, and about 1.13 to about 2.26 rad absorbed by the lower large bowel. Such levels of radiation exposure from the above dose range are not expected to cause acute or chronic effects to the patient. In addition, since there is no absorption of the isotope once the device 10 empties from the stomach, it is believed that the radiation exposure would subsequently be essentially confined to the small bowel and large bowel walls.

According to a nonlimiting embodiment of the invention, the core material 18 may be labeled with a radioactive isotope using an evaporation technique. For example, a radioactive isotope may be applied to the core material 18 through application and subsequent evaporation of an aqueous phase of the isotope. In particular, the aqueous phase of the isotope may be applied to the core material 18 and thereafter the liquid therein may be allowed to evaporate leaving behind the isotope which concentrates in the core material 18. For this type of labeling process, the core material 18 is preferably formed of an absorbent material. This labeling process is believed to be isotope-independent and compatible with all liquid isotopes that are known and used as tracers in the art. Particular but nonlimiting radioactive isotopes for use as a tracer for labeling the core material 18 include thallium-201, gallium-67, and indium-111 (each with a half-life of approximately 3 days). The isotopes may be obtained from any suitable source. Gallium citrate is a notable source for gallium-67 due to its relatively low cost and lower radiation exposure.

According to another nonlimiting aspect of the invention, the sealing material 16 may comprise a malleable material suitable for passing through the gastrointestinal tract in a manner similar to food. A preferred sealing material 16 comprises paraffin wax enclosed inside a gelatin capsule 12/14. It is within the scope of the invention that the device 10 may consist of only the core material 18 and the sealing material 16, consist of only the core material 18, the sealing material 16 and the capsule 12/14, or comprise these components in addition to other additional components.

In investigations leading to the present invention, production of a device 10 of a type represented in FIG. 1 included the following steps. However, such steps should be understood to be illustrative and not limiting to the scope of the invention.

In preparation for the investigations, radioactivity of an aqueous solution comprising a radioactive isotope was estimated. Gallium-67 citrate was used as the radioactive isotope for the investigations. A drop of the desired radioactive aqueous solution was placed on a bandage or similarly suitable substrate and allowed to dry. The substrate having the isotope thereon was then sealed and measured in a dose calibrator. This process was used to determine the approximate amount of isotope in a single drop of the aqueous solution of radioactive isotope so as to estimate the number of drops needed to produce the device under investigation.

In a second step, the core material 18 was prepared. In the investigations, a single grain of rice was utilized as the core material 18, and therefore the following discussion will refer to a rice grain as the core material 18. The rice grain was moistened with clean or sterile water and placed in the center of a five-centimeter diameter watch glass covered with non-stick aluminum foil. A very small amount (one drop or less) of a dark color food dye was placed onto the rice grain using a TB syringe and needle. The resulting color promoted positioning of the rice grain at a later stage in the production process. The required number of drops of the aqueous solution comprising the isotope as determined in the proceeding estimation step were then added to the grain of rice and the liquid was allowed to evaporate. For this purpose, the watch glass was placed on a low-level heat source to promote evaporation of the liquid. While the isotope did not cause radioactive release, evaporation of the liquid phase was performed in a ventilation hood. The estimated target amount of isotope was determined by the number of drops that were used on the rice grain. Once the estimated target activity (about 0.05 to 0.15 millicuries) of isotope was applied, the grain of rice was allowed to dry and then placed in a clean test tube. The radioactivity of the rice grain was measured in a dose calibrator. If more radioactivity was needed, the rice grain was returned to the watch glass and additional drops of the aqueous solution were added until the desired activity was reached.

The rice grain was allowed to completely dry on the heated, foil-covered watch glass. A small beaker was about half filled with a suitable sealing material 16, and the sealing material 16 was allowed to melt completely on the heat source. In these investigations, paraffin wax was utilized as the sealing material 16, and therefore the following discussion will refer to an experimental procedure that utilized paraffin wax as the sealing material 16.

Using a clean disposable dropper, a 00-sized gelatin capsule (utilized as the body 14) was filled two-thirds to three-quarters full with melted paraffin wax and allowed to partially cool. When the paraffin wax contacting the surface of the gelatin capsule began to turn opaque and solidify, an indentation at the top of the gelatin capsule began to appear. Tweezers were used to place one end of the rice grain into the center of the indentation. The rice grain was then pushed vertically into the soft paraffin wax using a standard syringe needle, for example 22 or 25 gauge, until the tip of the rice grain was just below the surface of the wax. The color of the food dye previously added to the rice was useful in positioning the rice grain in the center of the capsule. Another drop or two of paraffin wax was added to seal the top of the gelatin capsule above the uppermost portion of the rice grain such that the rice grain was fully encapsulated and surrounded by the wax. As the paraffin wax cooled, additional drops of wax were added if necessary to fill the cavity as the paraffin wax contracted. Alternatively or in addition to relying on the naturally forming indentation in the wax, a cavity in the paraffin wax could be made for the rice grain by placing a thin disposable pipette into the soft wax contained in the gelatin capsule, and then the pipette removed and the rice grain placed into the resulting cavity. The capsule was then filled and topped off with more melted paraffin wax. Once the wax had sufficiently cooled, the body of the gelatin capsule was closed and sealed with a cap and the final radioactivity was measured with a dose calibrator.

Devices manufactured according to the above process were determined to be stable in agitated room temperature water for over twelve hours. Although the gelatin capsule dissolved, its paraffin wax contents remained solid. The paraffin wax contents were also determined to be stable for over three hours in agitated water in a temperature ranging between 37 and 45 degrees centigrade, well above expected physiologic temperatures for humans. Although the paraffin wax may have become softened, it remained intact with the rice grain inside. At temperatures between 55 and 60 degrees centigrade, the paraffin wax melted exposing the rice grain. Since this temperature was well above the normal levels of a patient, the paraffin/rice combination was believed to be considered stable within the human body.

Figure 2:
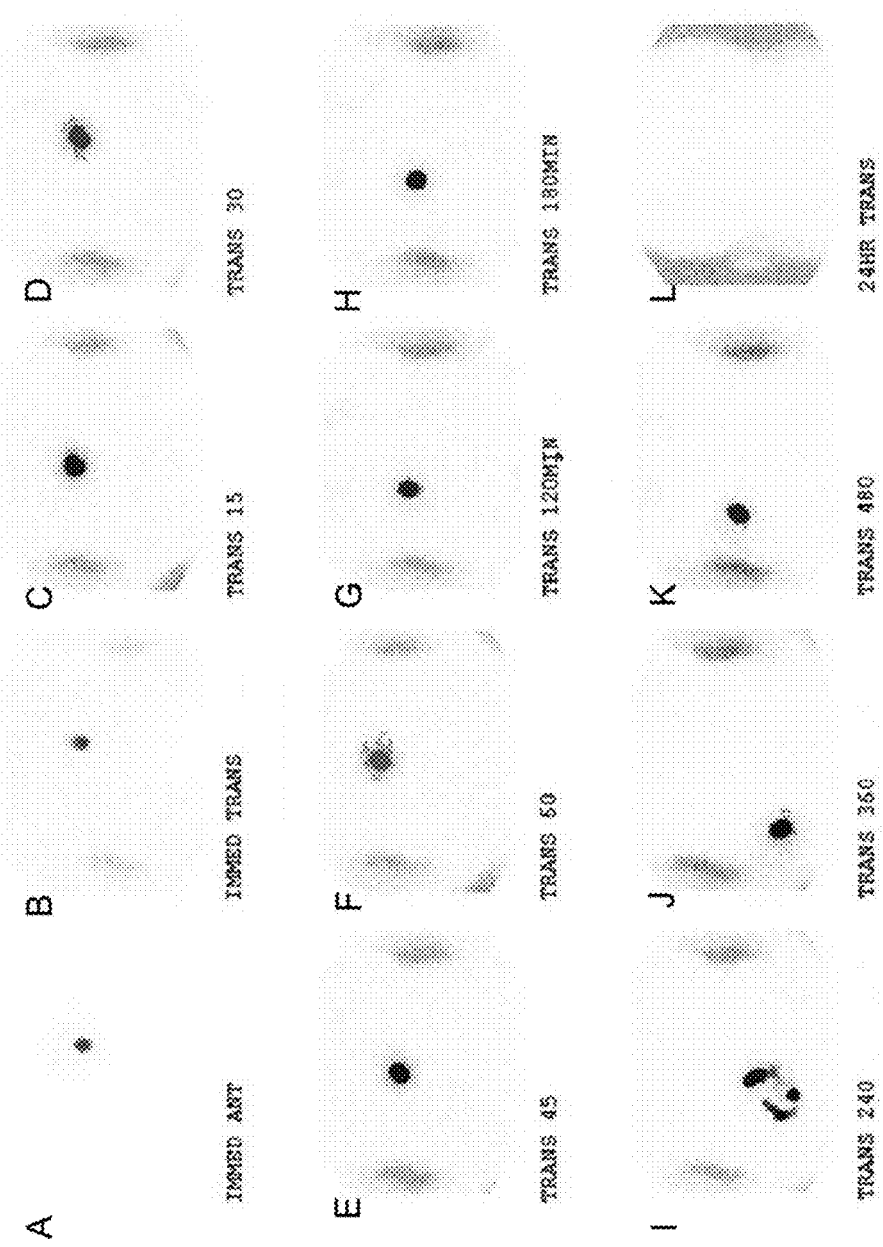
FIGS. 2 and 3 represent images of the gastrointestinal tract of two different volunteers taken during investigations that utilized traceable devices of the type represented in FIG. 1.
Figure 3:
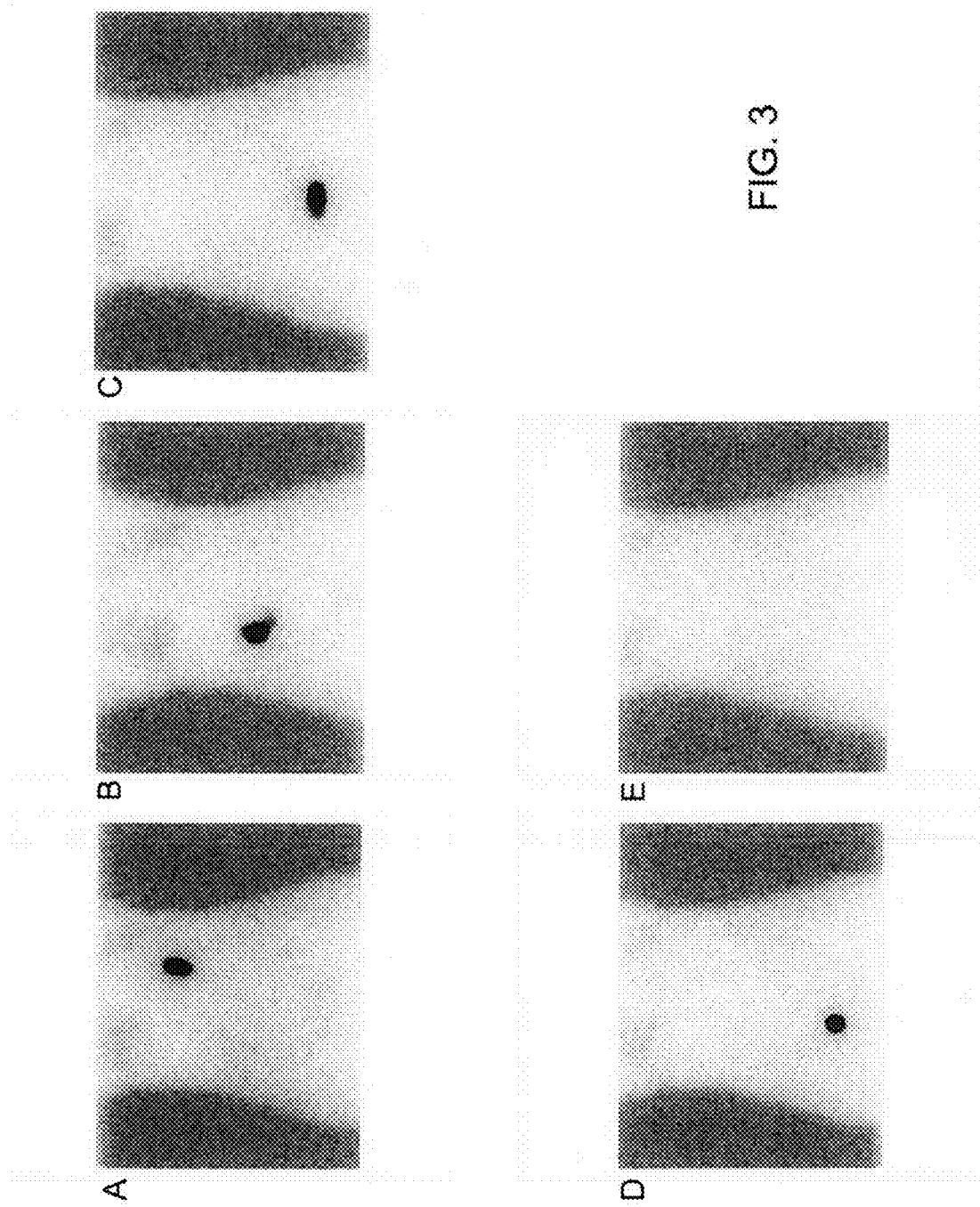

During further investigations leading to the present invention, devices produced according to the above process was individually orally administered to volunteers with a glass of water, after which imaging was immediately commenced over the abdomen. Images were obtained with a standard nuclear medicine gamma camera while the volunteer was in the supine position with arms either at the volunteer's side or above the volunteer's head using a five-minute acquisition (or 250,000 counts, whichever came first) with a medium energy collimator and a sheet source behind the volunteer to promote anatomic location. Images were subsequently obtained at two, four, six, and eight hours after ingestion. On the following days, images were obtained at approximately twenty-four, thirty-two, forty-eight, fifty-six, seventy-two, eighty, and ninety-six hours or until the capsule had been excreted. The location of the device was followed throughout the gastrointestinal tract and its location was documented at various times. Imaging was concluded for an individual volunteer if the device was excreted at any time (no longer visualized). A log sheet of bowel movement dates and times was kept by the volunteer for the duration of the study. Small bowel transit time was determined from the time that the capsule appeared to empty from the stomach to the time that it appeared within the ascending colon. Subsequent images identified the device as being in the ascending colon, transverse colon, descending colon, or sigmoid colon. FIGS. 2 and 3 represent images obtained for two of the volunteers during the investigations. These images show that the core material within each device remained as a point source throughout the entirety of the gastrointestinal tract. FIG. 2 represents the location of a device 10 (depicted as a dark circle) within the body of one of the volunteers immediately after administration (Images A and B), and 15 minutes (Image C), 30 minutes (Image D), 45 minutes (Image E), 60 minutes (Image F), 120 minutes (Image G), 180 minutes (Image H), 240 minutes (Image I), 360 minutes (Image J), 480 minutes (Image K), and 24 hours (Image L) after administration. The device 10 was observed to be within the stomach in images B-F, in the small bowel in images G-I, in the ascending colon in image J, in the hepatic flexure in image K, and excreted from the body in image L. FIG. 3 represents the location of a device 10 (depicted as a dark circle) within the body of another of the volunteers immediately after administration (Image A), and 3 hours (Image B), 4.5 hours (Image C), 6 hours (Image D), and 24 hours (Image E) after administration. In FIG. 3, the device 10 is located in the stomach in image A, in the small bowel in images B-D, and excreted from the body in image E.

In view of the above investigations, devices as described herein were concluded to provide effective tracers comprising a relatively small amount of a radioactive isotope that was capable of measuring the transit time along any portion of the bowel. The devices were found to be non-reactive, non-digestible, inexpensive, and easy to swallow, and have the potential to be used either alone or in combination with a standard nuclear medicine gastric emptying study. The devices also provided a reliable point source which promoted ease of imaging.

While the invention has been described in terms of specific embodiments, it is apparent that other forms could be adopted by one skilled in the art. For example, the physical configuration of the device 10 could differ from that shown, and materials and processes/methods other than those noted could be used. Therefore, the scope of the invention is to be limited only by the following claims.

The invention claimed is:

1. A traceable device comprising:
   a core material comprising a radioactive isotope visible with a gamma imaging process, wherein the core material is a single grain of rice and the radioactive isotope is thallium-201, gallium-67, and indium-111; and
   a sealing material substantially insoluble in gastrointestinal fluids and fully encapsulating the core material, wherein the sealing material comprises paraffin wax and prevents the core material from being dispersed in a human body after the device is administered orally to a patient and is present in a gastrointestinal tract of the patient.

2. The traceable device of claim 1, wherein the radioactive isotope is present in the core material in an amount that provides a dosage of about 0.05 millicuries to less than 0.2 millicuries.

3. The traceable device of claim 1, wherein the core material comprises a radio-opaque material visible with an x-ray imaging process.

4. The traceable device of claim 1, further comprising a second core material comprising a radio-opaque material visible with an x-ray imaging process, the sealing material fully encapsulating the second core material.

5. The traceable device of claim 1, further comprising a capsule encapsulating the sealing material and the core material and defining a body of the device, the capsule being substantially soluble in the gastrointestinal fluids.

* * * * *